United States Patent [19]
Lo et al.

[11] Patent Number: 4,594,189
[45] Date of Patent: Jun. 10, 1986

[54] PROCESS FOR PREPARING 3-PHENOXY-1-AZETIDINES AND CARBOXAMIDE DERIVATIVES

[75] Inventors: Young S. Lo, Richmond; Richard P. Mays, Ashland, both of Va.

[73] Assignee: A. H. Robins Company, Inc., Richmond, Va.

[21] Appl. No.: 511,077

[22] Filed: Jul. 6, 1983

[51] Int. Cl.$^4$ .................................... C07D 705/04
[52] U.S. Cl. ................................................ 260/239 A
[58] Field of Search .................................. 260/239 AR

[56] References Cited

U.S. PATENT DOCUMENTS

| | | | |
|---|---|---|---|
| 3,094,518 | 6/1963 | Testa et al. | 260/239 AR |
| 4,031,221 | 6/1977 | Helsley et al. | 424/267 |
| 4,226,861 | 10/1980 | Cale, Jr. | 260/239 AR |
| 4,379,151 | 4/1983 | Cale, Jr. | 260/239 AR |

OTHER PUBLICATIONS

Anderson, Jr., et al., J. Org. Chem., vol. 37, No. 24, (1972) pp. 3953–3955.
Dehmlow, et al., *Phase Transfer Catalysis*, Verlag Chemie, Weinheim, 1980, pp. 86–93.
Starks, et al., *Phase Transfer Catalysis*, Academic Press, N.Y., 1978, pp. 128–138.

*Primary Examiner*—Donald G. Daus
*Assistant Examiner*—William A. Teoli, Jr.

[57] ABSTRACT

An improved process is disclosed for preparing 3-phenoxyazetidines which utilizes a phase transfer catalyst to add the phenoxy group to azetidine blocked in the 1-position by a diphenylmethane group and utilizes a stabilizing tertiary amine base to prevent dimerization during hydrogenolysis to remove the blocking group. The crude product containing diphenylmethane may be used without purification to prepare 3-phenoxy-1-azetidinecarboxamides.

7 Claims, No Drawings

PROCESS FOR PREPARING 3-PHENOXY-1-AZETIDINES AND CARBOXAMIDE DERIVATIVES

BACKGROUND OF THE INVENTION

1. Field of Invention

The present invention relates to improved methods of preparing 3-phenoxyazetidines and their 1-carboxamide derivatives. The 3-phenoxyazetidines and 3-phenoxy-1-azetidinecarboxamides have pharmacological activity and use in the pharmaceutical field.

2. Information Disclosure Statement

The preparation of 3-phenoxyazetidines by hydrogenolysis of the corresponding 3-phenoxy-1-(α-methylbenzyl)azetidine or 1-diphenylmethyl-3-phenoxyazetidine is disclosed in U.S. Pat. No. 4,379,151. In that disclosure, 1-diphenylmethyl-3-phenoxyazetidine is derived by reacting phenol and sodium amide followed by reaction of the resulting phenolate with 1-diphenylmethyl-3-methanesulfonyloxyazetidine and the compounds have anorexigenic activity.

Anderson, A. G. and Lok, R. in J. Org. Chem. 37, 3953 (1972) disclosed preparation of 1-benzhydryl-3-methoxy (or ethoxy) azetidine via reaction of 1-diphenylmethyl-3-methanesulfonyloxyazetidine with methyl or ethyl alcohol.

The preparation of certain N-loweralkyl-3-phenoxy-1-azetidinecarboxamides which are useful as anticonvulsants from reaction of 3-phenoxyazetidines and isocyanates is disclosed in U.S. Pat. No. 4,226,861.

The preparation of 3-phenoxy-1-azetidine carboxamides is disclosed in copending application U.S. Ser. No. 409,476 filed Aug. 19, 1982. The compounds have anticonvulsant properties as demonstrated by the same methods as in U.S. Pat. No. 4,226,861

The preparation of N-formyl and N-hydroxymethyl-3-phenoxy-1-azetidinecarboxamides having anticonvulsant activity utilizing certain of the 3-phenoxy-1-azetidine carboxamides in reaction with formic acid or formaldehyde is disclosed in copending application U.S. Ser. No. 414,101 filed Sept. 2, 1982. The compounds have anticonvulsant properties as demonstrated by the same methods as in U.S. Pat. No. 4,226,861.

Features of the method of the present invention absent in the prior art are at least as follows:

(a) The 1-diphenylmethyl-3-phenoxyazetidine precursors are novelly prepared in the present invention from a phenol, alkali metal base and 1-diphenylmethyl-3-alkane (or benzene) sulfonyloxyazetidine using a phase transfer catalyst such as tetrabutylammonium bromide, and (b) Hydrogenolysis of the 1-diphenylmethyl-3-phenoxyazetidine to remove the protecting group and to produce the 3-phenoxyazetidine in a mixture with diphenylmethane by-product is conducted in the presence of an azetidine-stabilizing amount of a tertiary organic base such as triethylamine to prevent formation of a dimerization product found in the practice of prior art methods, which dimer has the following general structure:

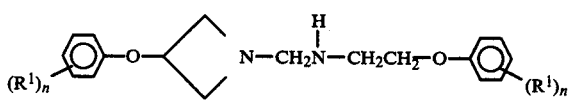
Interfering Dimer A

Both features a and b promote high yields and in addition, when the azetidine-stabilizing tertiary organic base is used, a mixture of 3-phenoxyazetidine and by-product diphenylmethane can be used without purification to prepare the carboxamides which can be isolated in relatively pure form by washing out the diphenylmethane. Prior art mixtures wherein no stabilizing amine is used contain about 15 parts by weight of the foregoing Dimer A to 85 parts by weight of the desired 3-phenoxyazetidine. As a result, when this mixture is not purified before reacting with methylisocyanate or nitrourea, in carboxamide preparation, a compound having the structure Dimer B results which is difficult to remove:

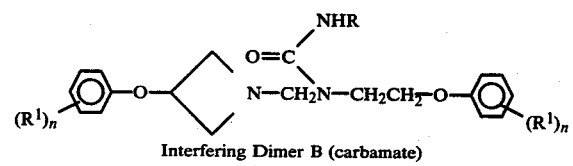
Interfering Dimer B (carbamate)

OBJECTS AND SUMMARY OF THE INVENTION

The invention is especially concerned with economical procedures for preparing 3-phenoxyazetidines and 3-phenoxy-1-azetidinecarboxamides which novelly employ catalysts or stabilizing agents to improve yields or prevent formation of certain contaminants. The 3-phenoxy-1-azetidines are anorexigenics as disclosed in the aforementioned U.S. Pat. No. 4,379,151 as well as chemical intermediates in the synthesis of 3-phenoxy-1-azetidinecarboxamides which have antidepressant activity as disclosed above and are useful in treating epilepsy.

The 3-phenoxy-1-azetidinecarboxamides prepared by the process of the present invention have the formula:

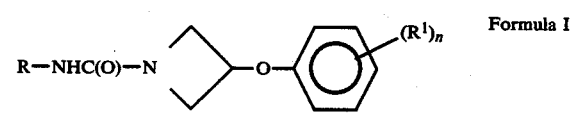
Formula I wherein R is selected from the group consisting of hydrogen or loweralkyl; $R^1$ is selected from the group consisting of hydrogen, fluoro, loweralkyl, loweralkoxy, trifluoromethyl, acetyl or aminocarbonyl, and n is selected from 1 to 3 inclusive wherein $R^1$ may be the same or different.

The 3-phenoxyazetidine precursors to compounds of Formula I have the formula

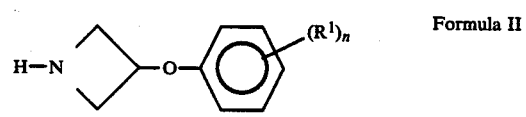
Formula II wherein $R^1$ and n are as defined above.

The 1-diphenylmethyl-3-phenoxyazetidine precursors to the Formula II compounds have the formula

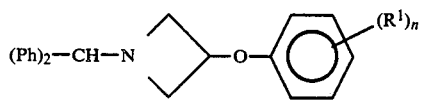

Formula III wherein $R^2$ and n are as defined above and Ph is phenyl or phenyl substituted by non-interfering radicals such as loweralkyl.

In the further definition of symbols in Formulas I, II, and III and where they appear elsewhere throughout this specification and in the claims, the terms have the following significance.

The term "loweralkyl" includes straight and branched chain hydrocarbon radicals of up to eight carbon atoms inclusive and is exemplified by such groups as methyl, ethyl, propyl, isopropyl, butyl, isobutyl, tertiary butyl, amyl, isoamyl, hexyl, heptyl, octyl and the like.

The term "loweralkoxy" has the formula O-loweralkyl.

The process of the invention is summarized by chemical equation in Chart 1. Obviously, the process may be stopped after step 1 to give compounds of Formula III or after step 2 to give compounds of Formula II or steps 2 and 3 alone may be employed to produce compounds of Formula I.

CHART I

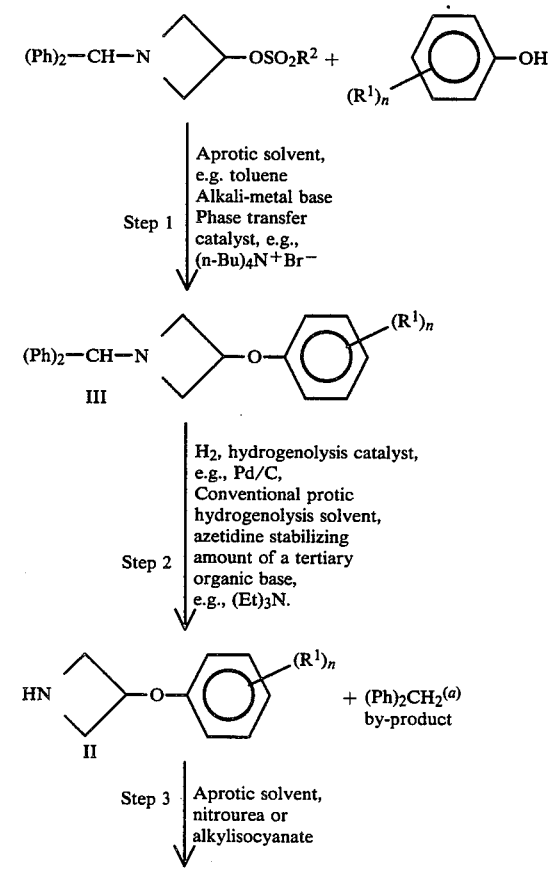

-continued
CHART I

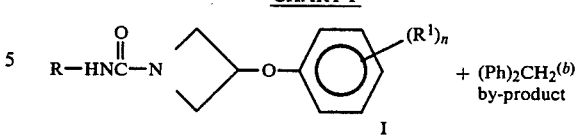

R = H or loweralkyl
[a] The diphenylmethane may be substantially or partially separated by washing with aprotic solvent such as toluene.
[b] The diphenylmethane is washed out with aprotic solvent unless it is desired to use the mixture ot prepare the N—formyl and N—hydroxymethyl-3-phenoxy-1-azetidine-carboxamides, mentioned above, from compounds wherein R = H.

It is therefore an object of the present invention to provide an improved process for the preparation of N-lower-alkyl-3-phenoxy-1-azetidinecarboxamides wherein the chemical intermediates are utilized more efficiently, leading to high overall yields.

Another object is to provide a method of producing 3-phenoxyazetidines free of polymerization products with minimal purification requirements.

Additional objects will be apparent to one skilled in the art and still other objects will become apparent hereinafter.

DETAILED DESCRIPTION OF THE INVENTION

A schematic of a detailed procedure illustrating the process for preparation of a mixture of a 3-phenoxyazetidine and by-product diphenylmethane, which process avoids formation of dimerization products found in practice of prior art methods, is presented in Chart II. A similar process schematic for conversion of the 3-phenoxyazetidines to 3-phenoxy-1-azetidinecarboxamides is presented in Chart III. Diphenylmethane may be wholly or partially separated before preparation of the carboxamides as indicated in Chart I.

The benzhydryl-sulfonyloxyazetidines used as starting materials in the preparation of the 1-benzhydryl-3-phenoxy azetidines may be prepared as described by Anderson & Lok, *J. Org. Chem.* 37, 3953 (1972) or as a solution as in the forepart of Example 1 below and if desired, such solution may be evaporated and the residue crystallized from a suitable solvent such as an isopropyl alcohol-water medium to give crystalline material. The preparation is illustrated in Chart IV.

The 1-benzhydryl-3-hydroxyazetidine hydrochlorides are prepared by the method of Anderson & Lok, ibid.

CHART II
Preparation of 3-Phenoxyazetidines

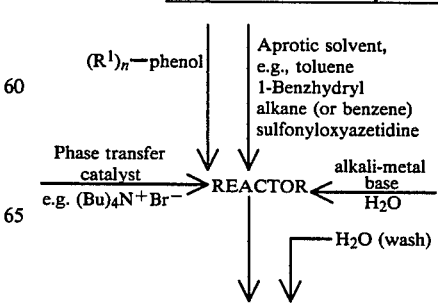

-continued
CHART II
Preparation of 3-Phenoxyazetidines

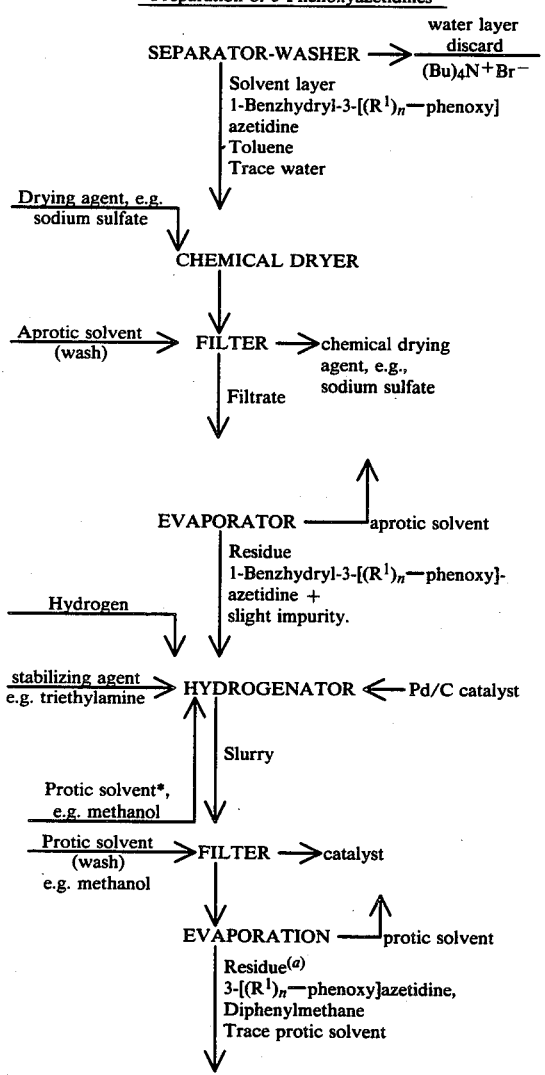

(a)The 3-[(R$^1$)$_n$phenoxy]azetidine in the mixture may optionally be converted to an addition salt and the salt washed with a solvent to remove diphenylmethane. The salt may be converted to the free base by proportioning in an appropriate solvent and aqueous basic solution.

CHART III
Conversion of 3-Phenoxyazetidines to
3-Phenoxy-1-azetidinecarboxamides

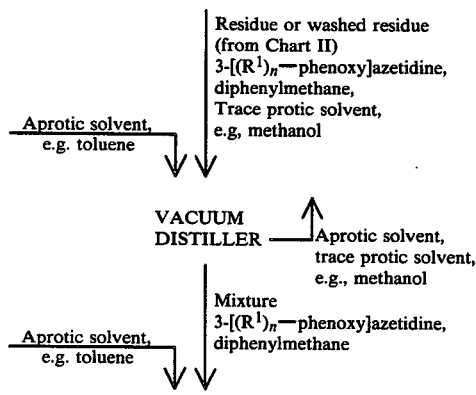

-continued
CHART III
Conversion of 3-Phenoxyazetidines to
3-Phenoxy-1-azetidinecarboxamides

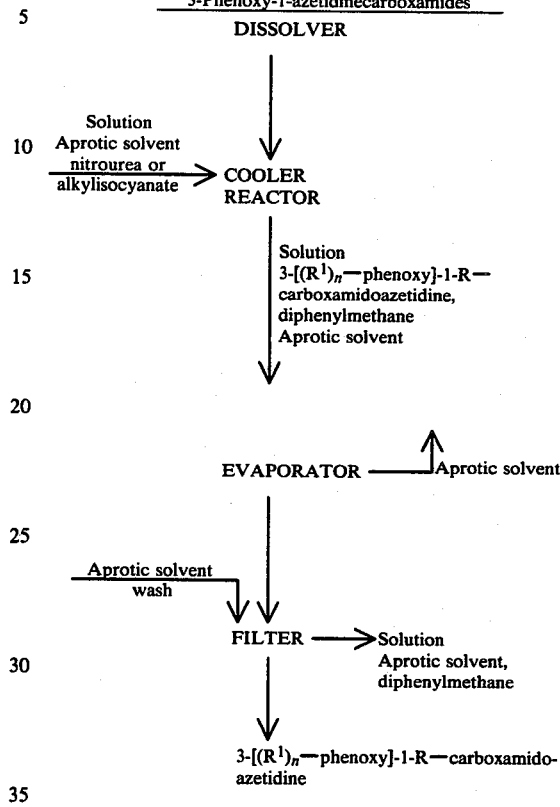

CHART IV
Preparation of Starting 1-Benzhydryl-3-
sulfonyloxyazetidines

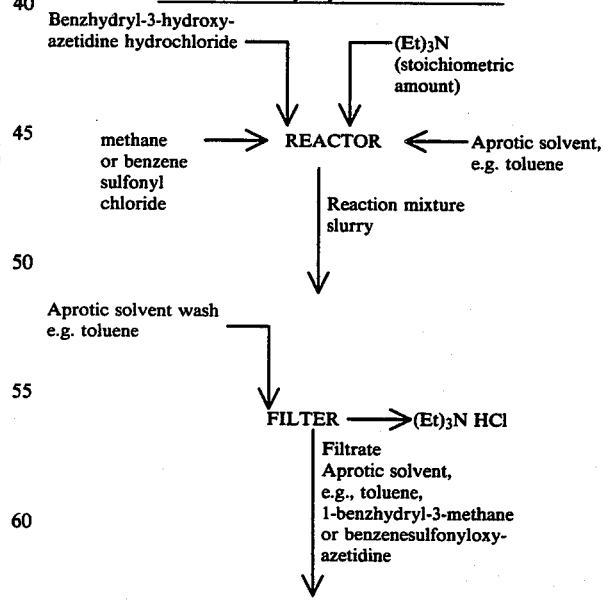

Briefly stated, the process of the invention is comprised of the following steps:

Step 1, reacting a 1-diphenylmethyl-3-alkane (or benzene) sulfonyloxyazetidine having the formula:

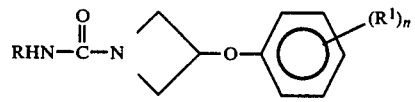

wherein Ph is phenyl or phenyl substituted by non-interfering radicals, $R^2$ is loweralkyl (1–8 C), phenyl or phenyl substituted by non-interfering radicals with a phenol having the formula:

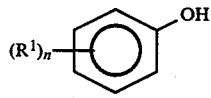

wherein $R^1$ and n are as defined under Formula I, together with an alkali-metal base and a phase transfer catayst, preferably tetra-n-butylammonium bromide in a suitable aprotic solvent; e.g., toluene, to give a solution comprised of a 1-diphenylmethyl-3-phenoxyazetidine having the formula:

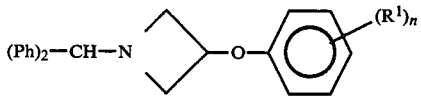

wherein Ph, $R^1$ and n are as defined above and thereafter washing the solution with water to remove the phase transfer catalyst, drying the solution and evaporating off the aprotic solvent.

Step 2, reacting the compound prepared in step 1 with hydrogen gas using a suitable hydrogenolysis catalyst, preferably palladium on carbon in a suitable protic solvent, preferably methanol or ethanol, together with an azetidine-stabilizing amount of a tertiary organic base, preferably triethylamine and preferably the amount of tertiary organic base being present in the range of 1 to 50 weight percent, preferably 1 to 10 weight percent based on the weight of the 1-diphenyl-methyl-3-phenoxyazetidine and thereafter filtering to remove the catalyst, evaporating to remove the protic solvent to give a residue comprised of by-product diphenylmethane and a 3-phenoxyazetidine having the formula:

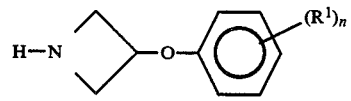

wherein $R^1$ and n have the starting values and optionally converting the 3-phenoxyazetidine in the mixture to an addition salt and washing out the diphenylmethane with an aprotic solvent to give a 3-phenoxyazetidine salt, and Step 3, reacting the 3-phenoxyazetidine in the mixture with diphenylmethane prepared in step 2 with nitrourea or loweralkyl isocyanate in an aprotic solvent, preferably toluene, to give a compound having the formula:

wherein R is hydrogen or loweralkyl and $R^1$ and n are as defined above and separating the diphenylmethane.

Prior to conducting step 3, a trace of protic solvent is preferably removed by azeotroping it off with the same aprotic solvent used in step 3.

The tertiary organic bases used to stabilize the azetidine in step 2 may vary widely and it is only necessary that they are sufficiently soluble in the protic hydrogenolysis solvent to protect the azetidine against dimerization and are illustrated by the following: triethylamine, trimethylamine, tri-n-propylamine, tri-n-butylamine, dimethylaniline, dimethylbenzylamine, N-methylmorpholine, N-methyl-piperidine and N-methyl-pyrrolidine and the like. Triethylamine and trimethylamine are preferred because of their volatility and low cost but volatility is not a prerequisite.

The following Examples 1–7 and preceding description and charts serve to illustrate the process of the invention. Examples 8 and 9 form basis for comparing with products of prior art procedures. The scope of the invention is not limited to the examples of the process, however.

EXAMPLE 1

1-(Diphenylmethyl)-3-[3-(trifluoromethyl)phenoxy azetidine.

Preparation of 1-benzhydryl-3-methanesulfonyloxyazetidine in solution

To a stirred solution of 41.33 g (0.15 mole) of N-diphenylmethyl-3-hydroxyazetidine hydrochloride, 42 ml (0.30 mole) of triethylamine in 250 ml of toluene was added 12 ml (0.15 mole) of methanesulfonylchloride dropwise over a 10 min period while maintaining the temperature between 4° to 12° C. After 1 hour, thin-layer chromatography (silica gel, 10% ethylacetate in methylene chloride) showed all starting materials had reacted. The mixture was filtered to remove triethylamine hydrochloride which was washed twice with toluene. The filtrate and washings were combined and measured about 450 ml of solution containing the title compound in theoretical (i.e. about 100%) yield.

To the foregoing toluene solution containing the 1-benzhydryl-3-methanesulfonyloxyazetidine was added 27.5 g (0.17 mole) of 3-trifluoromethylphenol, 2.4 g of tetrabutylammonium bromide, 24 g (0.3 mole) of sodium hydroxide and 24 ml of water and the mixture was stirred vigorously and heated to reflux under nitrogen atmosphere for 2.5 hr. The toluene layer was separated, washed once with water, dried over sodium sulfate and evaporated to give an oil residue. The oil was seeded and subjected to vacuum with an oil pump for about 15 hr. The solid cake obtained contained 49.7 g (86.6%) of the title compound. A portion of the solid cake was dissolved in isopropanol with brief heating. Water was added to cloud point and the mixture was seeded and cooled to cause crystallization. White solid was collected by filtration and washed with 50% aqueous isopropanol and dried under vacuum overnight.

NMR showed slight contamination by silicon oil. The melting point found was 82.5°–84° C.

Analysis: Calculated for $C_{23}H_{20}NOF_3$: C,72.05; H,5.26; N,3.65. Found: C,71.62; H,5.29; N,3.61.

EXAMPLE 2

When in the procedure of Example 1, equal molar amounts of the following are substituted for 3-trifluoromethylphenol:
phenol,
2-(trifluoromethyl)phenol,
4-(trifluoromethyl)phenol,
2-(carboxamido)phenol,
3-(carboxamido)phenol,
4-(carboxamido)phenol,
4-methylphenol,
4-methoxyphenol,
3,5-dimethoxyphenol,
3-fluorophenol, and
4-acetylphenol,
there are obtained:
1-(diphenylmethyl)-3-(phenoxy)azetidine,
1-(diphenylmethyl)-3-[2-(trifluoromethyl)phenoxy]azetidine,
1-(diphenylmethyl)-3-[4-(trifluoromethyl)phenoxy]azetidine,
3-[2-(carboxamido)phenoxy]-1-(diphenylmethyl)azetidine,
3-[3-(carboxamido)phenoxy]-1-(diphenylmethyl)azetidine,
3-[4-(carboxamido)phenoxy]-1-(diphenylmethyl)azetidine,
1-(diphenylmethyl)-3-[4-(methyl)phenoxy]azetidine,
1-(diphenylmethyl)-3-[4-(methoxy)phenoxy]azetidine,
1-(diphenylmethyl)-3-[3,5-(dimethoxy)phenoxy]azetidine,
1-(diphenylmethyl)-3-[3-(fluoro)phenoxy]azetidine, and
3-[4-(acetyl)phenoxy]-1-(diphenylmethyl)azetidine.

EXAMPLE 3

3-[3-(Trifluoromethyl)phenoxy]azetidine (and N-cyclohexylsulfamate salt).

1-(Diphenylmethyl)-3-[3-(trifluoromethyl)phenoxy]azetidine, 60 g (0.156 mole), 6 g of 5% palladium-on-carbon hydrogenolysis catalyst, 6 ml of triethylamine and 240 ml of ethanol were shaken under 20–40 psig hydrogen pressure at 60° C. in a Parr bottle for 4 hr, at which time hydrogen uptake ceased. The mixture was filtered to remove the catalyst, using ethanol to wash the filter cake. Toluene was added to the filtrate and this mixture was concentrated first under the reduced pressure of a water aspirator and then under high vacuum provided by an oil pump to give 60.96 g of clear oil which was a mixture of the title compound in quantitative yield, diphenylmethane by-product and a trace of ethanol and toluene. The N-cyclohexylsulfamate salt, prepared from a small portion of the mixture by reacting with hexylsulfamic acid in isopropyl alcohol and recrystallizing from the same solvent, melts at 123°–125° C.

EXAMPLE 4

When in the procedure of Example 3, the following are substituted for 1-(diphenylmethyl)-3-[3-(trifluoromethyl)phenoxy]azetidine:
1-(diphenylmethyl)-3-(phenoxy)azetidine,
1-(diphenylmethyl)-3-[2-(trifluoromethyl)phenoxy]azetidine,
1-(diphenylmethyl)-3-[4-(trifluoromethyl)phenoxy]azetidine,
3-[2-(carboxamido)phenoxy]-1-(diphenylmethyl)azetidine,
3-[3-(carboxamido)phenoxy]-1-(diphenylmethyl)azetidine,
3-[4-(carboxamido)phenoxy]-1-(diphenylmethyl)azetidine,
1-(diphenylmethyl)-3-[4-(methyl)phenoxy]azetidine,
1-(diphenylmethyl)-3-[4-(methoxy)phenoxy]azetidine,
1-(diphenylmethyl)-3-[3,5-(dimethoxy)phenoxy]azetidine,
1-(diphenylmethyl)-3-[3-(fluoro)phenoxy]azetidine, and
3-[4-(acetyl)phenoxy]-1-(diphenylmethyl)azetidine,
there are obtained:
3-(phenoxy)azetidine,
3-[2-(trifluoromethyl)phenoxy]azetidine,
3-[4-(trifluoromethyl)phenoxy]azetidine,
2-(3-azetidinyloxy)benzamide,
3-(3-azetidinyloxy)benzamide,
4-(3-azetidinyloxy)benzamide,
3-[4-(methyl)phenoxy]azetidine,
3-[4-(methoxy)phenoxy]azetidine,
3-[3,5-(dimethoxy)phenoxy]azetidine,
3-[3-(fluoro)phenoxy]azetidine, and
3-[4-(acetyl)phenoxy]azetidine.

EXAMPLE 5

3-[(3-Trifluoromethyl)phenoxy]-1-azetidinecarboxamide.

A mixture containing 5.6 g (0.026 mole) of 3-[3-(trifluoromethyl)phenoxy]azetidine free base and accompanying diphenylmethane by-product and a trace of methanol, all from Example 3, was dissolved in toluene and vacuum distilled, removing the trace of methanol during removal of the toluene. The residue was redissolved in 10 ml of toluene and the solution was cooled in an ice bath. To the cooled solution was added dropwise a solution of 1.54 ml (0.026 mole) of methyl isocyanate in 2 ml of toluene with stirring. The ice bath was removed a few minutes after addition of methyl isocyanate was complete and the mixture was stirred overnight. The mixture solidified and was thereafter subjected to low pressure with an oil vacuum pump to remove any unreacted methyl isocyanate. The white solid was placed on a suction filter and rinsed with toluene. Weight of the title compound was 6.3 g (88%).

EXAMPLE 6

When in the procedure of Example 5, the following are reacted with methyl isocyanate:
3-(phenoxy)azetidine,
3-[2-(trifluoromethyl)phenoxy]azetidine,
3-[4-(trifluoromethyl)phenoxy]azetidine,
2-[3-azetidinyloxy)benzamide,
3-(3-azetidinyloxy)benzamide,
4-(3-azetidinyloxy)benzamide,
3-[4-(methyl)phenoxy]azetidine,
3-[4-(methoxy)phenoxy]azetidine,
3-[3,5-(dimethoxy)phenoxy]azetidine,
3-[3-(fluoro)phenoxy]azetidine, and
3-[4-(acetyl)phenoxy]azetidine, there are obtained:
3-(phenoxy)-1-azetidinecarboxamide,
3-[2-(trifluoromethyl)phenoxy]-1-azetidinecarboxamide,
3-[4-(trifluoromethyl)phenoxy]-1-azetidinecarboxamide,
3-[2-(aminocarbonyl)phenoxy]-1-azetidinecarboxamide,
3-[3-(aminocarbonyl)phenoxy]-1-azetidinecarboxamide,
3-[4-(aminocarbonyl)phenoxy]-1-azetidinecarboxamide,
3-[4-(methyl)phenoxy]-1-azetidinecarboxamide,
3-[4-(methoxy)phenoxy]-1-azetidinecarboxamide,
3-[3,5-(dimethoxy)phenoxy]-1-azetidinecarboxamide,
3-[3-(fluoro)phenoxy]-1-azetidinecarboxamide, and
3-[4-(acetyl)phenoxy]-1-azetidinecarboxamide.

EXAMPLE 7

3-[3-(Trifluoromethyl)phenoxy]-1-azetidinecarboxamide.

A solution of 6 fold molar excess nitrourea and 3-[3-(trifluoromethyl)phenoxy]azetidine in a 50-50 vol. % mixture of methylene chloride and absolute ethyl alcohol is stirred at room temperature for 48 hr. The mixture is filtered. The filtrate is evaporated to dryness and the residue is partitioned between equal volumes of methylene chloride and water. The water layer is extracted 3 times with methylene chloride. The methylene chloride extracts are combined and evaporated to dryness. The residue is washed with a mixture of 1 vol. of methylene chloride to 20 volumes of toluene and filtered. The precipitate is recrystallized from ethanol/water to give pale yellow crystals. The crystals are triturated with a mixture of 2 volumes methylene chloride to 20 volumes of toluene for 2 hr. White crystals of title compound are obtained, m.p. 151°–152° C.

COMPARATIVE EXAMPLE 8

Following the procedure of Example 3 but omitting triethylamine, 1-(diphenylmethyl)-3-[3-(trifluoromethyl)phenoxy]azetidine was subjected to hydrogenolysis under the same conditions. The mixture was filtered and the filtrate was evaporated to give an oil residue. Mass spectroscopy showed the presence of material having the molecular weight corresponding to the desired product 3-[3-(trifluoromethyl)phenoxy]azetidine and dimerized impurity having a molecular weight of 435 having the structure of

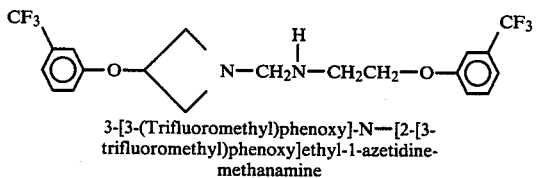

3-[3-(Trifluoromethyl)phenoxy]-N—[2-[3-trifluoromethyl)phenoxy]ethyl-1-azetidine-methanamine From the $C^{13}$NMR spectrum obtained on the mixture, it was estimated from the integrations of the signals that the mixture contained about 15 parts by weight of the dimer to 85 parts by weight of the desired product.

COMPARATIVE EXAMPLE 9

Following the procedure of Example 5, the residue obtained in Example 8 was reacted with methyl isocyanate and the product of the reaction was isolated as a white solid. The white solid contained about 95 wt. % 3-[(3-trifluoromethyl)phenoxy]-1-azetidinecarboxamide. An impurity amounting to about 5 wt. % of the product, the reaction product of the dimer impurity in the starting residue with methyl isocyanate was isolated by thin-layer chromatography and found to have the structure of

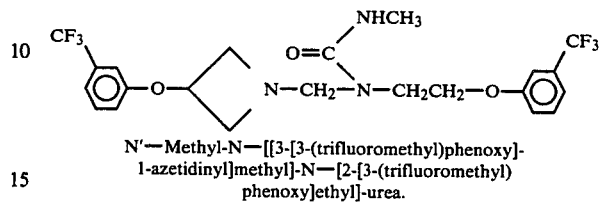

N'—Methyl-N—[[3-[3-(trifluoromethyl)phenoxy]-1-azetidinyl]methyl]-N—[2-[3-(trifluoromethyl)phenoxy]ethyl]-urea.

What is claimed is:
1. A process for preparing 3-phenoxyazetidines having the formula:

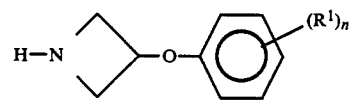

wherein $R^1$ is selected from the group consisting of hydrogen, fluoro, loweralkyl, loweralkoxy, trifluoromethyl, acetyl or aminocarbonyl, and n is selected from 1 to 3 inclusive wherein $R^1$ may be the same or different, which comprises reacting a 1-diphenylmethyl-3-phenoxyazetidine having the formula:

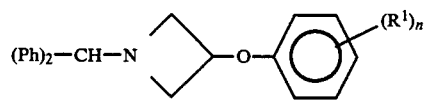

wherein Ph is phenyl or phenyl substituted by a non-interfering group and $R^1$ and n are as defined above with hydrogen gas with a hydrogenolysis catalyst in a protic solvent together with an azetidine stabilizing tertiary organic base inert hydrogenolysis.

2. The process of claim 1 wherein the amount of tertiary organic base used is in the range of 1 to 50 weight percent based on the weight of the 1-diphenyl-methyl-3-phenoxyazetidine.

3. The process of claim 1 wherein the tertiary organic base used is triethylamine.

4. The process of claim 1 wherein the tertiary organic base used is trimethylamine.

5. The process of claim 1 wherein the starting azetidine is 1-diphenylmethyl-3-[3-(trifluoromethyl)phenoxy]azetidine and the product is 3-[3-(trifluoromethyl)phenoxy]azetidine.

6. A process for preparing 3-phenoxy-1-azetidinecarboxamides having the formula:

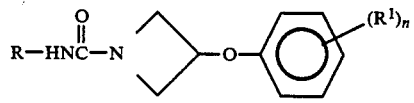

wherein;
R is selected from the group comprised of hydrogen and loweralkyl, $R^1$ is selected from the group consisting of hydrogen, fluoro, loweralkyl, loweralkoxy, trifluoromethyl, acetyl or aminocarbonyl, and n is selected from 1 to 3 inclusive wherein $R^1$ may be the same or different, which comprises the steps of Step 1, reacting a compound selected from the group having the formula:

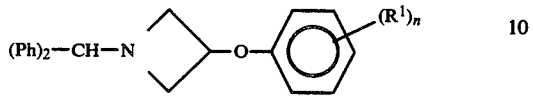

wherein Ph is phenyl or phenyl substituted by a non-interfering group and $R^1$ and n are as defined above with hydrogen gas using a hydrogenolysis catalyst in a protic solvent together with an azetidine-stabilizing tertiary organic base inert hydrogenolysis, and thereafter filtering to remove the catalyst, evaporating to remove the protic solvent to give a residue comprised of by-product diphenylmethane and a 3-phenoxyazetidine having the formula:

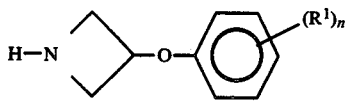

wherein $R^1$ and n have the starting values,

Step 2, reacting the 3-phenoxyazetidine in the mixture with diphenylmethane prepared in step 1 with nitrourea or loweralkyl isocyanate in a solvent to give the desired 3-phenoxy-1-azetidinecarboxamide and separating out the diphenylmethane.

7. The process of claim 6 wherein the amount of tertiary organic base used is in the range of 1 to 50 weight percent based on the weight of the 1-diphenylmethyl-3-phenoxyazetidine.

* * * * *

UNITED STATES PATENT AND TRADEMARK OFFICE
CERTIFICATE OF CORRECTION

PATENT NO. : 4,594,189
DATED : Jun. 10, 1986
INVENTOR(S) : Young S. Lo, et al

It is certified that error appears in the above–identified patent and that said Letters Patent are hereby corrected as shown below:

Col. 2, line 39, change "antidepressant" to read --anticonvulsant--

Signed and Sealed this

Third Day of March, 1987

Attest:

DONALD J. QUIGG

Attesting Officer

Commissioner of Patents and Trademarks